United States Patent
Akerfeldt

(10) Patent No.: US 6,663,653 B2
(45) Date of Patent: Dec. 16, 2003

(54) ADJUSTABLE RADIAL ARTERY COMPRESSOR

(75) Inventor: Dan Akerfeldt, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 09/956,244

(22) Filed: Sep. 20, 2001

(65) Prior Publication Data
US 2003/0055453 A1 Mar. 20, 2003

(51) Int. Cl.$^7$ ................................................ A61F 5/00
(52) U.S. Cl. ........................ 606/203; 602/5; 128/878
(58) Field of Search ........................ 128/846, 885, 128/886, DIG. 25, 878, 879; 600/29–31; 606/203; 602/5, 20, 21, 62, 64

(56) References Cited

U.S. PATENT DOCUMENTS

| | | | | |
|---|---|---|---|---|
| 2,533,924 A | * | 12/1950 | Foley | 128/885 |
| 3,050,064 A | * | 8/1962 | Moore | 128/327 |
| 3,203,421 A | * | 8/1965 | Bialick | 128/885 |
| 4,798,199 A | | 1/1989 | Hubbard et al. | 128/87 |
| 4,988,355 A | * | 1/1991 | Leveen | 606/158 |
| 5,601,597 A | | 2/1997 | Arrowood et al. | 606/203 |
| 5,989,270 A | * | 11/1999 | Suh | 606/157 |
| 2002/0017303 A1 | * | 2/2002 | Single | 128/848 |

* cited by examiner

*Primary Examiner*—Michael A. Brown
(74) *Attorney, Agent, or Firm*—Foley & Lardner

(57) ABSTRACT

Following a catheterization of the radial artery in the forearm, the flow of blood through to puncture wound has to be stopped. An adjustable radial artery compressor (1) according to the invention comprises a support arm (2) provided with a support pad (5), a compressor arm (3) provided with a compression pad (6), and a pressure-adjusting means (7, 9, 10) for adjusting the distance between the support pad (5) and the compression pad (6). When the adjustable radial artery compressor (1) is arranged on the forearm of a patient, the support pad (5) bears against a well-defined area at the upside of the radius bone while the compression pad (6) presses against a well-defined area at the underside of the radius bone. With the pressure-adjusting means (7, 9, 10) the compression pressure can be adjusted with high precision, and due to the well-defined contact surfaces, which minimize the risk of vein stasis, the compression pressure is constant irrespective of any movement of the hand or forearm.

43 Claims, 3 Drawing Sheets

ADJUSTABLE RADIAL ARTERY COMPRESSOR

FIELD OF THE INVENTION

The present invention relates to a radial artery compression system, and more particularly to an adjustable radial artery compressor, with which the compression force applied on the radial artery can be adjusted so that haemostasis can be obtained without occluding the artery. Further, when arranged around the forearm of a patient, the present radial artery compressor ensures that the same compression pressure is applied on the radial artery irrespectively of the position of the forearm, which reduces the immobility time for the patient.

BACKGROUND OF THE INVENTION

Following an invasive medical procedure, such as catheterisation or similar invasive medical procedure, the flow of blood through the puncture wound has to be stopped, so that haemostasis can begin as soon and fast as possible after the completion of the invasive medical procedure. Several devices have been suggested that facilitate and accelerate this haemostasis by providing a compression pressure that compresses blood vessels in various parts of the body to stop flow of blood therethrough.

In the case of radial artery catheterisation, several radial artery occluders have been developed that stop the flow of blood through the puncture wound in the wrist by applying a compression force that occludes the radial artery. An illustrative example of such a pressure-applying device is disclosed in U.S. Pat. No. 5,601,597. This known artery occluder comprises a wrist splint, an adjustable securing strap attached to one end of the splint, and an adjustable pressure strap attached to other end of the splint and provided with a pressure pad. When the artery occluder is mounted around the forearm of a patient, the wrist splint extends along the distal end of the forearm and the back of the wrist and hand, the securing strap extends around the palm of the hand, and the pressure strap extends around the distal end of the forearm, with the pressure pad being positioned over the puncture wound in the radial artery. During use of this occluder, the adjustable pressure strap is slowly tightened over the bleeding wound in the radial artery until the flow of blood in the radial artery has stopped at the wound. This aids haemostasis in the wound, but allows the ulnar artery to deliver enough blood to ensure tissue viability. In addition, the adjustable securing strap is tightened around the palm of the hand to immobilize the wrist.

In U.S. Pat. No. 5,601,597 the inventors emphasize on the importance of immobilizing the wrist joint since movement of the wrist may cause stretching and contraction of the wounded tissue. Stretching and contraction of the tissue surrounding the puncture wound can prevent clotting and thereby causing delay in haemostasis of an arterial puncture. However, although the device according to U.S. Pat. No. 5,601,597 effectively prevents a patient from bending his/her wrist, it is still relatively easy for the patient to twist the forearm, i.e. to rotate the forearm. As will be described below, when the forearm is twisted, the two bones in the forearm, the ulnar bone and the radius bone, will cross over. Since the device above stops the flow of blood through the radial artery by compressing the radial artery between the pressure pad and the radius bone, this cross-over of the ulnar and radius bones will change the magnitude of the compression force on the radial artery and may also change the position of the radial artery itself. Consequently, a twist of the forearm may delay the haemostasis process and even cause more severe problems, such as reopening of the puncture wound. In practise, the patient is therefore immobilized during the compression period, i.e. the time for the haemostasis to occur.

Another disadvantage with the device according to U.S. Pat. No. 5,601,597, and also with similar devices that are mounted around the wrist and forearm so that the forearm is surrounded by a strap and/or a splint, arises from the fact that the compression force applied on the radial artery, i.e. the force on the underside of the forearm, equals the force applied on the upside of the forearm. Due to the superficial location of the veins at the upside of the forearm, this type of design may lead to vein stasis. Vein stasis for a longer period can be both painful for the patient and cause vein thrombosis. As is done in U.S. Pat. No. 5,601,597, this problem can be reduced by letting a splint or support plate distribute the reaction force onto the upside of the forearm over a large area, thereby reducing the compression pressure on the veins. However, since the compression device normally remains seated over the puncture wound for several hours, the flow of blood through the veins is still restricted for a long time period, and the risk of vein stasis is therefore not completely eliminated.

In the vast majority of prior art designs in which the compression force is applied by straps that are secured in tension by buckles or Velcro, it is very difficult to fine-tune the compression pressure. In use, this means that such a compression device is arranged around the wrist and forearm of a patient and is then left untouched in this position for the whole compression period, i.e. the same compression pressure is applied during the whole compression period. However, since it is known that a higher compression pressure is required in the beginning of the compression period than in the end of the compression period, this procedure is not ideal. Without the possibility to fine-tune the compression pressure, it is also difficult to accommodate individual differences among different patients, i.e. there is a risk that a higher compression pressure than needed is applied on the puncture wound, which increases the risk of vein stasis.

Finally, as mentioned above, when the radial artery is occluded, only the ulnar artery delivers blood to the hand. Although the ulnar artery alone normally is capable of deliver enough blood to the hand to ensure tissue viability, obviously it would be advantageous if the compression pressure could be fine-tuned in such a way that haemostasis is obtained without occluding the radial artery completely.

SUMMARY OF THE INVENTION

An improved radial artery compressor is needed, which overcomes the disadvantages of the prior art devices.

A first object of the present invention is therefore to provide an adjustable radial artery compressor that provides a possibility to fine-tune the compression pressure over the puncture wound following an invasive medical procedure such as catheterisation.

A second object of the present invention is to provide a radial artery compressor with which the compression pressure applied over the puncture wound is constant irrespective of any movements of the hand or forearm.

A third object of the present invention is to provide a radial artery compressor that eliminates or minimizes the risk of vein stasis in the superficial veins at the upside of the forearm.

These objects are achieved with an adjustable radial artery compressor as defined in claim 1. Preferred embodiments of the adjustable radial artery compressor according to the invention are defined in the dependent claims.

An embodiment of the adjustable radial artery compressor according to the present invention includes basically two arms, a support arm and a compression arm, which form a C-shaped clamp. The support arm and the compression arm are pivotally connected in a hinge joint in such way that the support arm extends behind the compression arm. In the opposite ends, i.e., the ends remote from the hinge joint, the support and compression arms are each provided with a pad. A clamping screw is threaded through the end of the extending support arm and is in contact with the compression arm. When the clamping screw is turned inwards, it presses against the compression arm, thereby controlling the distance between the compression pad on the compression arm and the support pad on the support arm. In use, the forearm of a patient is arranged between the compression pad on the compression arm and the support pad on the support arm so that the radial artery is compressed between the radius bone and the compression pad. By turning the clamping screw inwards or outwards, it is therefore possible to adjust the compression pressure on the radial artery with high precision.

DETAILED DESCRIPTION OF THE INVENTION

Figure 1:
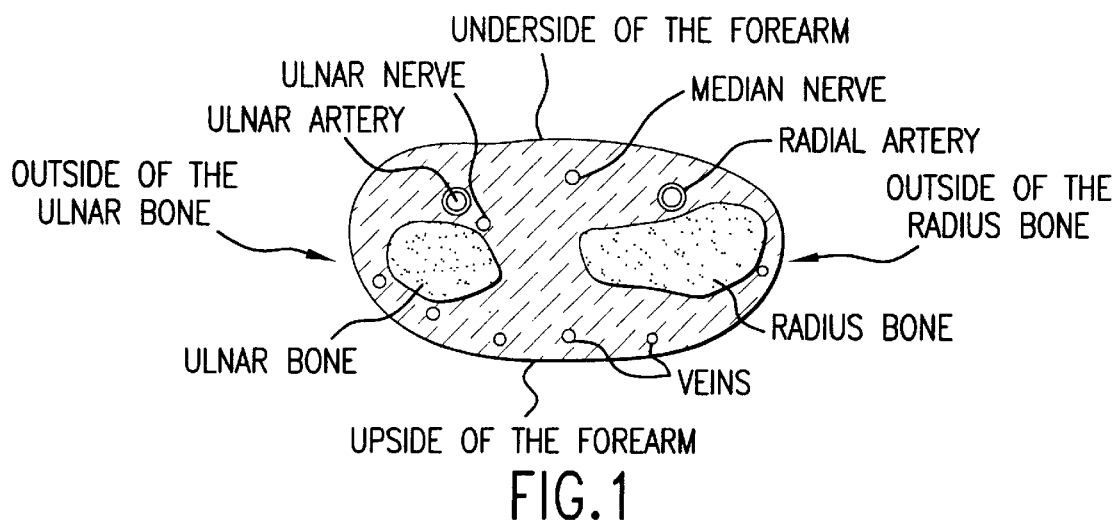
FIG. 1 is a schematic cross-sectional view of the wrist anatomy.

As background information, FIG. 1 shows schematically in cross-section the wrist anatomy with the ulnar and radius bones, the ulnar and radius arteries, the ulnar and median nerves, and the superficial veins at the upside of the forearm. In the description below, several references are made to different sides of the forearm, and also these terms are indicated in FIG. 1.

Figure 2:
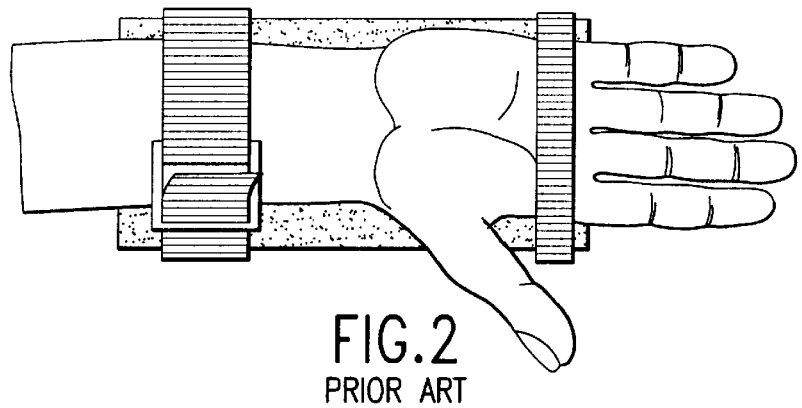
FIG. 2 is a top view of a prior art artery occluder.
Figure 3:
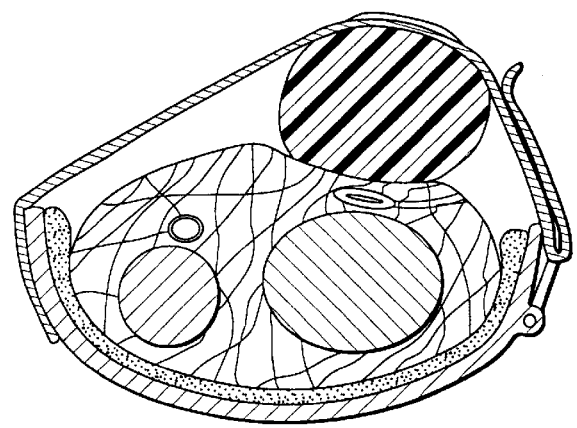
FIG. 3 is a cross-sectional view of the artery occluder of FIG. 2 arranged around the forearm of a patient.
Figure 4:
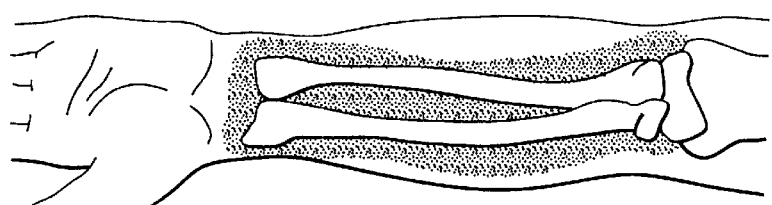
FIG. 4 shows schematically the forearm bones in a first position.
Figure 5:
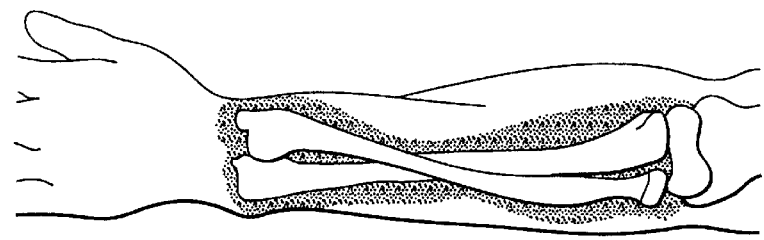
FIG. 5 shows schematically the forearm bones in a second position.

FIG. 2 is schematic top view of the combined radial artery occluder and wrist splint as disclosed in U.S. Pat. No. 5,601,597. FIG. 3 shows that when this prior art device is arranged around the forearm of a patient, the radial artery is compressed between the radius bone and a pressure pad provided underneath a pressure strap mounted on the wrist splint. In FIG. 3 the positions of the forearm bones, the ulnar bone and the radius bone, correspond to the positions shown in FIG. 4. When the forearm is twisted, the forearm bones will cross over and take the positions schematically shown in FIG. 5. Accordingly, the pressure applied on the radial artery by this known artery occluder will vary depending on whether or not the forearm is twisted.

Figure 6:
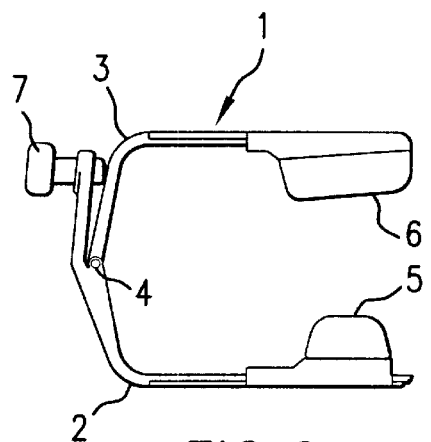
FIG. 6 is a side view of the adjustable radial artery compressor according to the present invention.
Figure 7:
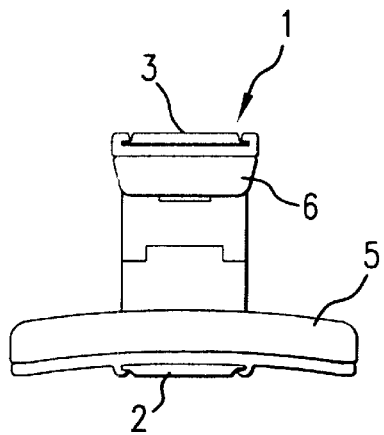
FIG. 7 is an end view of the adjustable radial artery compressor of FIG. 6.

First with reference to FIG. 6 and FIG. 7, where an adjustable radial artery compressor 1 according to the present invention basically includes two arms, a support arm 2 and a compression arm 3, which form a C-shaped clamp. The support arm 2 and the compression arm 3 are pivotally connected in a hinge joint 4 in such a way that the proximal end of the support arm 2 extends behind the compression arm 3. At the distal end, i.e., the end remote from the hinge joint 4, the inside of the support arm 2 is provided with a support pad 5, and an opposing compression pad 6 is provided on the distal end of the compression arm 3. A clamping screw 7 is threaded through the proximal end of the support arm 2 in such a way that the front end of the clamping screw 7 is in contact with the compression arm 3. By screwing the clamping screw 7 inwards or outwards, the distance between the support pad 5 and the compression pad 6 can adjusted, thereby controlling the compression pressure applied on the radial artery.

Figure 8:
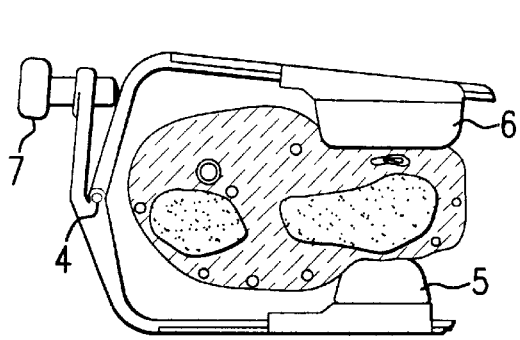
FIG. 8 is a cross-sectional view of the adjustable radial artery compressor according to the present invention arranged around the forearm of a patient.

As seen in FIG. 8, when this C-shaped clamp is arranged on the forearm of a patient, the support pad 5 will bear against the upside of the forearm while the compression part 6 will press against the underside of the forearm, thereby compressing the radial artery between the radius bone and the compression pad 6. By turning the clamping screw 7, the compression pressure on the intermediate radial artery can be carefully adjusted so that haemostasis can be obtained without completely occluding the artery. With the adjustable radial artery compressor 1 according to the invention it is therefore easy to adjust the compression pressure during the compression period, i.e. to gradually reduce the compression force exerted by the compression arm 3 by turning the clamping screw 7, so that an optimal compression pressure is applied.

As can be seen from FIG. 8, there exists a clearance between the support arm 2 and the upside of the forearm. A similar clearance exists also between the compression arm 3 and the underside of the forearm. In this embodiment of the present invention, the C-shaped clamp is therefore only in contact with two well-defined areas at the underside and upside of the forearm. This means that a twisting movement of the forearm will not affect the position of the adjustable radial artery compressor 1. Consequently, the same compression pressure is applied on the radial artery whether or not the ulnar and radius bones are crossed over.

As also seen in FIG. 8, with the present design of the radial artery compressor 1, the support pad 5 distributes the reaction force on the upside of the forearm over a well-defined area of tissue overlaying the radius bone. This tissue contains almost no sensitive or delicate structures, which makes this area suitable to bear the compression force. Consequently, none, or at least very few, of the superficial veins at the upside of the forearm will experience any compression pressure, which eliminates the risk of vein stasis. Also the ulnar and median nerves as well as the ulnar artery remain unaffected during compression of the radial artery, which minimizes the discomfort for the patient.

Figure 9:
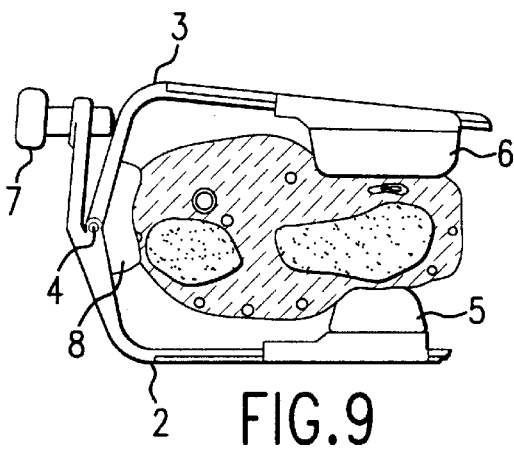
FIG. 9 shows a first, preferred alternative embodiment of the adjustable radial artery compressor according to the present invention.

In FIG. 9 a preferred embodiment of the invention is shown. Here, the adjustable radial artery compressor 1 has been provided with an extra pad 8 at the hinge joint 4. When the compressor 1 is arranged on the forearm of a patient, this extra pad 8 constitutes an extra support for the forearm, which further ensures the correct positioning of the compressor 1 during the whole compression period. This extra pad 8 does not negatively interfere with the above-mentioned features and advantages of the present invention. In the preferred embodiment, the support pad 5 can slide along the support arm 2 and the compression pad 6 can slide along the compression arm 3. The adjustable radial artery compressor according to the present invention is therefore capable of accommodating different wrist widths and anatomies. The compression pad 6 should be sized to cover a well-defined area overlaying the radial artery, and preferably with enough oversize to allow some misplacement by the user, e.g. 100 mm². The support pad 5 is, in this example, 15 mm wide and 80 mm long and slightly curved to uniformly distribute the compression pressure over a well-defined area of tissue overlaying the radius bone. Furthermore, both the support pad and the compression pad, or at least the compression pad, could be made of a transparent material, thereby providing the possibility of direct visual observation of the puncture wound, which facilitates the positioning of the radial artery compressor.

Although the present invention has been described with reference to specific embodiments, also shown in the appended drawings, it will be apparent for those skilled in the art that may variations and modifications can be done within the scope of the invention as described in the specification and defined in the following claims. For example, although a clamping screw is a convenient means to adjust the compression pressure, there exist other ways to accomplish this pressure adjustment, such as spring-loaded means, cogged or toothed means, or pneumatic means.

Further, since the main objective of the radial artery compressor according to the invention is to compress the radial artery between the radius bone and a compression pad by pressing on two well-defined, restricted contact surfaces at the underside and upside of the radius bone, it is also possible to let the support and compression arms form a rectangular clamp. In this case, there is no need for a hinge joint that connects the support and compression arms. Furthermore, it is also conceivable to keep the C-shape of the clamp, but exclude the hinge joint and replace the clamping screw above, which is threaded through the support arm and presses against the compression arm, with another clamping screw that is threaded through the distal end of the compression arm and attached to the compression pad, thereby adjusting to distance between the compression pad and the support pad, without changing the distance between the support arm and the compression arm.

Figure 10:
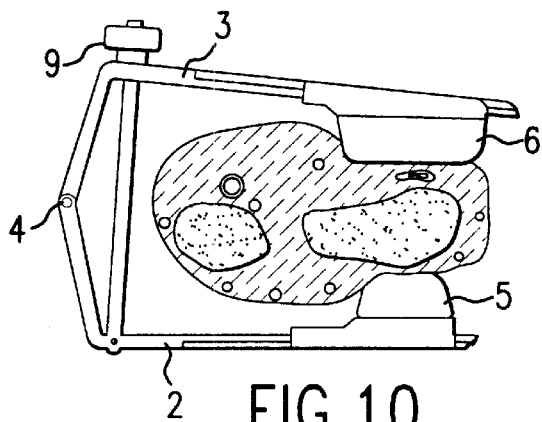
FIG. 10 shows a second alternative embodiment of the adjustable radial artery compressor according to the present invention.

In FIG. 10 an alternative embodiment of the present radial artery compressor is shown. In this embodiment, the support arm 2 and the compression arm 3 are still connected by the hinge joint 4, but the clamping screw 7, which in FIG. 9 presses against the backside of the compression arm, has been replaced with a tightening screw 9, which is threaded through the compression arm 3 and attached to the support arm 2. The tightening screw in this alternative embodiment is approximately perpendicular to the support and compression arms and could be arranged wither at the distal end of the support and compression arms or, as in FIG. 10, at the same side of the forearm as the hinge joint.

Figure 11:
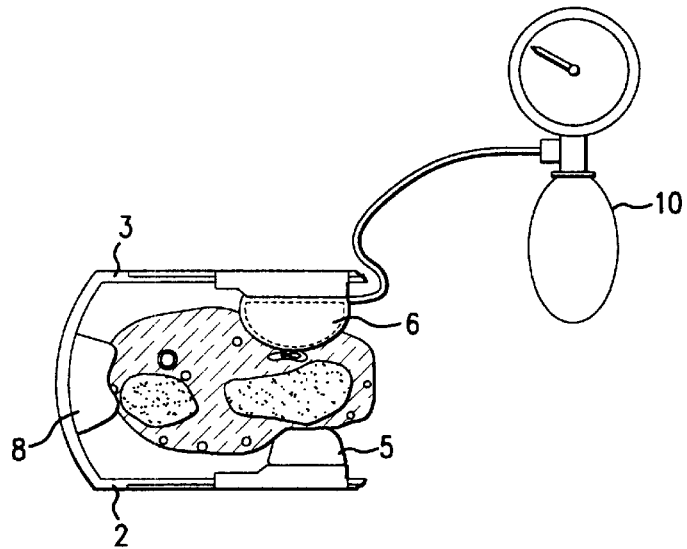
FIG. 11 shows a third alternative embodiment of the adjustable radial artery compressor according to the present invention.

FIG. 11 shows how the distance between the support pad 5 and the compression pad 6, and thereby the pressure on the radial artery, could be adjusted by means of a pneumatic device 10 connected to the compression pad 6. In this embodiment, the compression pad 6 is inflatable and is expanded by the pneumatic device 10. As an alternative, or as a complement, also the support pad 5 could be inflatable and could be expanded with the same pneumatic device 10, or with a separate pneumatic device. In FIG. 11 there is no hinge joint, but it is of course possible to combine the pneumatic device 10 with a clamping screw 7 of the type shown in FIG. 9 or with a tightening screw 9 of the type shown in FIG. 10.

What is claimed is:

1. Adjustable radial artery compressor for stopping the flow of blood through a puncture wound in a radial artery of a patient following a catheterisation procedure, comprising:

a support arm provided with a support pad;

a rigid compression arm connected to the support arm and provided with a compression pad; and a pressure adjuster configured to adjust a distance between the support pad and the compression pad, wherein the compressor is configured so that, when the compressor is arranged on a forearm of the patient, the support pad bears against a well-defined area at an upside of a radius bone and the compression pad presses against a well-defined area at an underside of the radius bone, thereby applying a compression pressure that compresses the radial artery between the compression pad and the radius bone, wherein the pressure adjuster is configured to adjust the compression pressure.

2. The adjustable radial artery compressor according to claim 1, wherein the support arm and the compression arm form a C-shaped clamp, the distal ends of which are provided with the support pad and the compression pad, respectively.

3. The adjustable radial artery compressor according to claim 2, wherein said C-shaped clamp is provided with an extra pad that, when the compressor is arranged on the forearm, bears against an outside of an ulnar bone.

4. The adjustable radial artery compressor according to claim 2, wherein the pressure adjuster is a pneumatic device connected to the compression pad, wherein the compression pad is inflatable, wherein the pneumatic device is configured to adjust the distance between the support pad and the compression pad by expanding the compression pad.

5. The adjustable radial artery compressor according to claim 2, wherein the support arm and the compression arm are pivotally connected with a hinge joint in such a way that the proximal end of the support arm extends behind the compression arm, and wherein said pressure adjuster is a clamping screw that is threaded through the proximal end of the support arm and contacts an outside of the compression arm, wherein the clamping screw is configured to adjust the distance between the support pad and the compression pad by turning the clamping screw.

6. The adjustable radial artery compressor according to claim 2, wherein the support arm and the compression arm are pivotally connected with a hinge joint in such a way that the proximal end of the support arm extends behind the compression arm, wherein the compression pad is inflatable, and wherein said pressure adjuster comprises:

a pneumatic device that is connected to the compression pad and configured to expand the compression pad; and a clamping screw that is threaded through the proximal end of the support arm and contacts an outside of the compression arm, wherein the pressure adjuster is configured to adjust the distance between the support pad and the compression pad by turning the clamping screw and expanding the compression pad.

7. The adjustable radial artery compressor according to claim 2, wherein the support arm and the compression arm are pivotally connected with a hinge joint, and wherein said pressure adjuster is a tightening screw that connects the support arm with the compression arm and is configured to adjust the distance between the support pad and the compression pad by turning the tightening screw.

8. The adjustable radial artery compressor according to claim 7, wherein the tightening screw connects the distal end of the support arm with the distal end of the compression arm.

9. The adjustable radial artery compressor according to claim 7, wherein the tightening screw is arranged at the same side of the forearm as the hinge joint.

10. The adjustable radial artery compressor according to claim 2, wherein the support arm and the compression arm are pivotally connected with a hinge joint, wherein the compression pad is inflatable, and wherein said pressure adjuster comprises:
  a pneumatic device that is connected to the compression pad and configured to expand the compression pad; and
  a tightening screw that connects the support arm with the compression arm,
  wherein the pressure adjuster is configured to adjust the distance between the support pad and the compression pad by turning the tightening screw and expanding the compression pad.

11. The adjustable radial artery compressor according to claim 1, wherein the support pad is slidably mounted on the support arm.

12. The adjustable radial artery compressor according to claim 1, wherein the compression pad is slidably mounted on the compression arm.

13. The adjustable radial artery compressor according to claim 1, wherein the compression pad is made of a transparent material.

14. The adjustable radial artery compressor according to claim 1, wherein the support pad is made of a transparent material.

15. An adjustable radial artery compressor, comprising:
  a support arm provided with a support pad;
  a rigid compression arm, a proximal portion of which is connected to a proximal portion of the support arm, provided with a compression pad, wherein the compressor is configured so that, when the compressor is arranged on a forearm of a patient, the support pad bears against a well-defined area at an upside of a radius bone and the compression pad presses against a well-defined area at an underside of the radius bone, thereby applying a compression pressure that compresses the radial artery between the compression pad and the radius bone; and
  a pressure adjuster connected to the proximal portion of at least one of the support arm and the compression arm, wherein the pressure adjuster is configured to adjust a distance between the support pad and the compression pad.

16. The adjustable radial artery compressor according to claim 15, wherein the support arm is provided with exactly one support pad and the compression arm is provided with exactly one compression pad.

17. The adjustable radial artery compressor according to claim 15, wherein the support arm and the compression arm are connected by a hinge.

18. The adjustable radial artery compressor according to claim 17, wherein the support pad and the compression pad are located approximately equidistant from the hinge.

19. The adjustable radial artery compressor according to claim 15, wherein the support arm is rigid, and wherein the support arm and the compression arm are not configured to bend when pressure is applied to the support pad and the compression pad.

20. The adjustable radial artery compressor according to claim 15, wherein the support arm and the compression arm are integrally connected.

21. The adjustable radial artery compressor according to claim 15, wherein the compressor is sized to accommodate a forearm of a patient.

22. An adjustable radial artery compressor, comprising:
  a support arm provided with a support pad;
  a compression arm, a proximal portion of which is connected to a proximal portion of the support arm, provided with a compression pad;
  a pressure adjuster connected to the proximal portion of at least one of the support arm and the compression arm; and
  an extra pad located approximately at a point of connection between the support arm and the compression arm,
  wherein the pressure adjuster is configured to adjust a distance between the support pad and the compression pad.

23. An adjustable radial artery compressor, comprising:
  a support arm provided with a support surface;
  a compression arm, a proximal portion of which is connected to a proximal portion of the support arm, provided with a compression pad; and
  a pressure adjuster connected to at least one of the support arm and the compression arm and configured to adjust a distance between the support surface and the compression pad,
  wherein the support surface is located at a distal end of the support arm and the compression pad is located at a distal end of the compression arm.

24. The adjustable radial artery compressor according to claim 23, wherein the support arm is provided with exactly one support surface and the compression arm is provided with exactly one compression pad.

25. The adjustable radial artery compressor according to claim 23, wherein the support arm and the compression arm are connected by a hinge.

26. The adjustable radial artery compressor according to claim 25, wherein the support surface and the compression pad are located approximately equidistant from the hinge.

27. The adjustable radial artery compressor according to claim 23, wherein the support arm and the compression arm are rigid and are not configured to bend when pressure is applied to the support surface and the compression pad.

28. The adjustable radial artery compressor according to claim 23, wherein the pressure adjuster is connected to the proximal portion of said at least one of the support arm and the compression arm.

29. The adjustable radial artery compressor according to claim 23, wherein the compressor is configured so that, when the compressor is arranged on a forearm of a patient, the support surface bears against a well-defined area at an upside of a radius bone and the compression pad presses against a well-defined area at an underside of the radius bone, thereby applying a compression pressure that compresses the radial artery between the compression pad and the radius bone.

30. The adjustable radial artery compressor according to claim 23, wherein the support arm and the compression arm are integrally connected.

31. The adjustable radial artery compressor according to claim 23, wherein the support surface includes a support pad.

32. The adjustable radial artery compressor according to claim 23, wherein the compressor is sized to accommodate a forearm of a patient.

33. An adjustable radial artery compressor, comprising:
   a support arm provided with a support surface;
   a compression arm, a proximal portion of which is connected to a proximal portion of the support arm, provided with a compression pad; and
   a pressure adjuster, having a member configured to turn, connected to at least one of the support arm and the compression arm, and configured to finely adjust a distance between the support surface and the compression pad by turning the member,
   wherein the compressor is sized to accommodate a forearm of a patient.

34. The adjustable radial artery compressor according to claim 33, wherein the support surface is located at a distal end of the support arm and the compression pad is located at a distal end of the compression arm.

35. The adjustable radial artery compressor according to claim 33, wherein the support arm is provided with exactly one support surface and the compression arm is provided with exactly one compression pad.

36. The adjustable radial artery compressor according to claim 33, wherein the support arm and the compression arm are connected by a hinge.

37. The adjustable radial artery compressor according to claim 36, wherein the support surface and the compression pad are located approximately equidistant from the hinge.

38. The adjustable radial artery compressor according to claim 33, wherein the support arm and the compression arm are rigid and are not configured to bend when pressure is applied to the support surface and the compression pad.

39. The adjustable radial artery compressor according to claim 33, wherein the pressure adjuster is connected to the proximal portion of said at least one of the support arm and the compression arm.

40. The adjustable radial artery compressor according to claim 33, further comprising an extra pad located approximately at a point of connection between the support arm and the compression arm.

41. The adjustable radial artery compressor according to claim 33, wherein the compressor is configured so that, when the compressor is arranged on the forearm of the patient, the support surface bears against a well-defined area at an upside of a radius bone and the compression pad presses against a well-defined area at an underside of the radius bone, thereby applying a compression pressure that compresses the radial artery between the compression pad and the radius bone.

42. The adjustable radial artery compressor according to claim 33, wherein the support arm and the compression arm are integrally connected.

43. The adjustable radial artery compressor according to claim 33, wherein the support surface includes a support pad.

* * * * *